US009605058B2

(12) United States Patent
Taylor et al.

(10) Patent No.: US 9,605,058 B2
(45) Date of Patent: Mar. 28, 2017

(54) ANTIBODIES AGAINST THE CXC-ELR FAMILY OF CHEMOKINES

(71) Applicant: GlaxoSmithKline LLC, Wilmington, DE (US)

(72) Inventors: Alexander Harrison Taylor, King of Prussia, PA (US); John Richard White, King of Prussia, PA (US); Yu Xu, King of Prussia, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 14/398,131

(22) PCT Filed: May 1, 2013

(86) PCT No.: PCT/US2013/038991
§ 371 (c)(1),
(2) Date: Oct. 31, 2014

(87) PCT Pub. No.: WO2013/166099
PCT Pub. Date: Nov. 7, 2013

(65) Prior Publication Data
US 2015/0110810 A1 Apr. 23, 2015

Related U.S. Application Data

(60) Provisional application No. 61/640,796, filed on May 1, 2012.

(51) Int. Cl.
*C07K 16/24* (2006.01)
*C07K 16/18* (2006.01)
*A61K 39/00* (2006.01)

(52) U.S. Cl.
CPC ............... *C07K 16/18* (2013.01); *C07K 16/24* (2013.01); *C07K 16/244* (2013.01); *A61K 2039/505* (2013.01); *C07K 2317/24* (2013.01); *C07K 2317/31* (2013.01); *C07K 2317/33* (2013.01); *C07K 2317/41* (2013.01)

(58) Field of Classification Search
None
See application file for complete search history.

(56) References Cited

U.S. PATENT DOCUMENTS

2006/0104971 A1  5/2006  Garber et al.
2008/0262203 A1  10/2008 Clegg et al.
2011/0229475 A1  9/2011  Clegg et al.

FOREIGN PATENT DOCUMENTS

WO  WO 2009/149189 A2  12/2009

OTHER PUBLICATIONS

Granziero et al. Adoptive immunotherapy prevents prostate cancer in a transgenic animal model, Eur. J. immunol. 29, 1127-1138, 1999.*
Byers T., What can randomized controlled trials tell us about nutrition and cancer prevention?, CA Cancer J. Clin. 49, 353-361, 1999.*
Co, M. S., et al.,: "Properties and pharmacokinetics of two humanized antibodies specific for L-selectin", Immunotechnology, vol. 4, No. 3-4, Mar. 1, 1999 (Mar. 1, 1999), pp. 253-266.
Isaacs, J. D., et al.: "A Therapeutic Human Igg4 Monoclonal Antibody That Depletes Target Cells in Humans", Clinical and Experimental Immunology, vol. 106, No. 3, Dec. 1, 1996 (Dec. 1, 1996), pp. 427-433.
Reddy, M. P., et al: "Elimination of Fc receptor-dependent effector functions of a modified IgG4 monoclonal antibody to human CD4", The Journal of Immunology, vol. 164, No. 4, Feb. 15, 2000 (Feb. 15, 2000), pp. 1925-1933.
S. Main, et al.: "A Potent Human Anti-Eotaxinl Antibody, CAT-213: Isolation by Phage Display and in Vitro and in Vivo Efficacy", Journal of pharmacology and experimental Therapeutics, vol. 319, No. 3, Dec. 1, 2006 (Dec. 1, 2006), pp. 1395-1404.
Salfeld Jochen G: "Isotype selection in antibody engineering", Nature Biotechnology, vol. 25, No. 12, Dec. 1, 2007 (Dec. 1, 2007), pp. 1369-1372.
Suitters, A. J., et al.,: "differential effect of isotype on efficacy of anti-tumor Necrosis factor alpha-chimeric antibodies in experimental septic shock", The Journal of Experimental Medicine, vol. 179, No. 3, Mar. 1, 1994 (Mar. 1, 1994), pp. 849-856.
Warncke, Max, et al.: "Different Adaptations of IgG Effector Function in Human and Nonhuman Primates and Implications for Therapeutic Antibody Treatment", Journal of Immunology, vol. 188, No. 9, 28 Mar. 2012 (Mar. 28, 2012), pp. 4405-4411.

* cited by examiner

*Primary Examiner* — Elly-Gerald Stoica
(74) *Attorney, Agent, or Firm* — William T. Han; Edward R. Gimmi; William R. Majarian

(57) ABSTRACT

The invention relates to antibodies which treat diseases in which human IL-8, Gro-alpha, Gro-beta, Gro-gamma, GCP-2, and/or ENA-78 are implicated.

5 Claims, 3 Drawing Sheets

SEQUENCE LISTING

<160> NUMBER OF SEQ ID NOS: 10

<210> SEQ ID NO 1
<211> LENGTH: 449
<212> TYPE: PRT
<213> ORGANISM: Artificial Sequence
<220> FEATURE:
<223> OTHER INFORMATION: PanELR Heavy Chain

<400> SEQUENCE: 1

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
        35                  40                  45

Gly Asp Leu Tyr Ser Gly Gly Tyr Thr Phe Tyr Ser Glu Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Asp Arg Thr Trp Phe Ala His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: PanELR Light Chain

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Glu Ser Tyr
            20                  25                  30

Leu Ser Trp Tyr Gln Gln Lys Pro Gly Lys Ala Pro Lys Leu Leu Ile
        35                  40                  45

Tyr Tyr Ala Thr Arg Leu Ala Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180             185             190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 449
<212> TYPE: PRT
<213> ORGANISM: Artificial Sequence
<220> FEATURE:
<223> OTHER INFORMATION: PanELR Fc Disabled Heavy Chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
        35                  40                  45

Gly Asp Leu Tyr Ser Gly Gly Tyr Thr Phe Tyr Ser Glu Asn Phe
50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Asp Arg Thr Trp Phe Ala His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
            325                 330                 335
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 4
<211> LENGTH: 446
<212> TYPE: PRT
<213> ORGANISM: Artificial Sequence
<220> FEATURE:
<223> OTHER INFORMATION: PanELR IgG4 (PE) Heavy Chain

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
            35                  40                  45

Gly Asp Leu Tyr Ser Gly Gly Tyr Thr Phe Tyr Ser Glu Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Asp Arg Trp Phe Ala His Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Glu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 5
<211> LENGTH: 446
<212> TYPE: PRT
<213> ORGANISM: Artificial Sequence
<220> FEATURE:
<223> OTHER INFORMATION: PanELR IgG4(PE)N297A Heavy Chain

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
        35                  40                  45

Gly Asp Leu Tyr Ser Gly Gly Tyr Thr Phe Tyr Ser Glu Asn Phe
    50                  55                  60

Lys Gly Arg Val Thr Met Thr Arg Asp Thr Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Asp Arg Thr Trp Phe Ala His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 6
<211> LENGTH: 446
<212> TYPE: PRT
<213> ORGANISM: Artificial Sequence
<220> FEATURE:
<223> OTHER INFORMATION: PanELR IgG4(PE)N297S Heavy Chain

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
        35                  40                  45

Gly Asp Leu Tyr Ser Gly Gly Gly Tyr Thr Phe Tyr Ser Glu Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
             85                  90                  95

Ala Arg Ser Gly Tyr Asp Arg Thr Trp Phe Ala His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Ser Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 7
<211> LENGTH: 1347
<212> TYPE: DNA
<213> ORGANISM: Artificial Sequence
<220> FEATURE:
<223> OTHER INFORMATION: Polynucleotide encoding PanELR Fc disabled
      Heavy Chain

<400> SEQUENCE: 7

```
caggtccagc tggtgcagag cggcgccgag gtgaagaagc ccggcgccag cgtgaaggtg    60
agctgcaagg ccagcggcta caccttcacc aactactgga tcgtgtgggt gaggcaggcc   120
cccggccagg gcctggagtg gatgggagac ctgtacagcg cggcggcta caccttctac   180
agcgagaact tcaagggcag ggtgactatg acccgggaca ccagcacctc taccgtgtac   240
atggagctga gcagcctgag gtcagaggat accgccgtgt actactgtgc caggagcggc   300
tacgacagga cttggttcgc ccactggggc cagggcaccc tggtgaccgt cagctcagcc   360
agcaccaaag gccccagcgt gttccccctg ctcccagca gcaaaagcac cagcggcggc   420
accgccgccc tgggctgcct ggtcaaggac tacttccccg agcccgtgac cgtgagctgg   480
aatagcggcg ccctgacaag cggcgtgcac accttccccg ccgtgctcca gtctagcggc   540
ctgtacagcc tgagcagcgt ggtgacagtg cctagcagca gcctgggcac ccagacctac   600
atctgcaacg tgaaccacaa gcccagcaac accaaggtgg acaagaaggt cgaacccaag   660
agctgcgaca agacccacac ctgcccacct tgccccgcac ccgaactcgc cggcgcccct   720
agcgtcttcc tgttcccacc caagcccaag gacaccctga tgatcagcag gaccccgag   780
gtgacctgcg tggtggtgga cgtgagccac gaggaccccg aggtgaagtt caactggtac   840
gtggacggcg tggaggtgca caacgccaag accaagccca gggaggagca gtacaactcc   900
acctacaggg tggtgagcgt gctgaccgtg ctgcaccagg actggctgaa cgggaaggag   960
tacaagtgca aggtgagcaa caaggccctg ccgcccca tcgagaaaac catcagcaag  1020
gccaaggcc agcccagaga gcctcaggtg tataccctgc ccccaagcag ggacgagctg  1080
accaagaacc aggtgagcct gacctgcctg gtgaagggct tctatcccag cgacattgcc  1140
gtggagtggg agagcaacgg acagcccgag aacaactaca agaccaccc cccgtcctg  1200
gatagcgacg gcagcttctt cctgtacagc aagctgaccg tggacaagag caggtggcag  1260
cagggcaacg tgtttagctg tagcgtgatg cacgaggccc tccacaacca ctacacccag  1320
aagtccctga gcctgagccc cggcaag                                    1347
```

<210> SEQ ID NO 8
<211> LENGTH: 1338
<212> TYPE: DNA
<213> ORGANISM: Artificial Sequence
<220> FEATURE:
<223> OTHER INFORMATION: Polynucleotide encoding PanELR IgG4 (PE) Heavy Chain

<400> SEQUENCE: 8

```
caggtgcagc tggtgcagag cggcgcagag gtgaagaaac ccggcgcttc cgtgaaggtg    60
agctgtaagg ccagcggcta caccttcacc aactactgga tcgtgtgggt gaggcaggcc   120
cccggccagg gcctggagtg gatgggcgac ctgtacagcg gggcggcta caccttctac   180
agcgagaact tcaagggcag ggtgaccatg actaggaca cctccaccag caccgtgtac   240
atggagctgt ccagcctgag gagcgaggac accgccgtgt attactgcgc ccggagcggc   300
tacgatagga cttggttcgc ccactggggc cagggcaccc tggtcaccgt gagcagcgct   360
agcaccaaag gccctagcgt gttccccctg gcccctgct ctaggagcac atctgagagc   420
acagccgccc tgggctgcct ggtgaaggac tactttcccg agcccgtgac cgtgtcttgg   480
aacagcggag cactcaccag cggcgtgcac accttccctg ccgtgctgca gagcagcggc   540
ctgtacagcc tgagcagcgt ggtgaccgtg ccaagcagca gcctgggcac caagacctac   600
```

```
acctgcaacg tggaccacaa gcccagcaac accaaggtgg acaagagggt ggagagcaaa    660
tacggacccc cctgcccccc ctgcccgcc cccgagtttg aaggaggccc cagcgtgttc      720
ctgttccccc ccaagcccaa ggacaccctg atgatcagca ggaccccga agtgacctgc     780 gtggtggtgg acgtgagcca ggaggacccc gaagtgcagt tcaactggta cgtggacggc    840
gtcgaggtgc acaacgccaa gaccaagccc agagaggagc agttcaacag cacctacagg    900
gtggtgtcag tgctcaccgt gctgcatcag gactggctga acggcaagga gtacaagtgc    960
aaggtcagca caagggcct gcccagcagc atcgagaaga ccatcagcaa ggccaagggc    1020
cagccaaggg agccccaggt ctataccctg cccccagcc aggaggagat gaccaagaac    1080
caggtgtccc tgacctgcct ggtcaaggc ttctacccca gcgacattgc cgtggagtgg    1140
gagagcaacg gccagcccga gaacaactac aagaccaccc cccccgtgct ggatagcgac    1200
gggagcttct tcctgtacag caggctgacc gtggacaaaa gcaggtggca ggagggcaac    1260
gtgttcagct gctccgtgat gcacgaggcc ctccacaatc actacaccca gaagagcctg    1320
agcctgtccc tgggcaag                                                  1338

<210> SEQ ID NO 9
<211> LENGTH: 1338
<212> TYPE: DNA
<213> ORGANISM: Artificial Sequence
<220> FEATURE:
<223> OTHER INFORMATION: Polynucleotide encoding PanELR IgG4(PE)N297A
      Heavy Chain

<400> SEQUENCE: 9
caggtgcagc tggtgcagag cggcgccgag gtgaagaagc ccggcgccag cgtgaaagtg    60
agctgcaagg ccagcggcta caccttcacc aactactgga tcgtgtgggt gaggcaggcc    120
cccggccagg gactggagtg gatgggcgac ctgtatagcg ggggaggcta caccttctac    180
agcgagaact tcaagggcag ggtgaccatg accaggaca ccagcaccag caccgtgtac    240
atggagctca gcagcctgag gagcgaggat acagccgtgt actattgcgc caggagcggc    300
tacgacagaa cctggttcgc ccactggggg cagggcaccc tcgtgactgt cagcagcgcc    360
agcaccaaag ccctctgt gttccccctg gcccctgta gcaggagcac cagcgagtca    420
accgccgccc tgggctgcct ggtgaaagac tacttccctg agcccgtgac cgtgagctgg    480
aatagcggcg cactgaccag cggcgtgcac acctttcccg ccgtgctgca gtctagcggc    540
ctgtacagcc tgagctcagt ggtgaccgtg cccagcagca gcctgggcac caagacctac    600
acctgcaacg tggaccacaa gcccagcaac accaaggtgg acaagcgggt ggaaagcaag    660
tacggccccc cttgcccccc ctgcccgca cccgagttcg agggcggccc aagcgtgttc    720
ctgtttcccc ccaagcccaa ggacaccctg atgatcagca ggaccccga ggtgacttgc    780 gtggtggtgg acgtgtccca ggaggacccc gaggtgcagt tcaactggta cgtggacggc    840
gtggaagtgc acaacgccaa gaccaagccc agggaggagc agttcgccag cacctacagg    900
gtggtcagcg tcctgaccgt gctgcaccag gactggctga acggcaagga gtacaagtgc    960
aaggtgagca caagggcct gcccagcagc atcgagaaga ccatcagcaa ggccaaggga    1020
cagcccaggg agccccaggt gtacacactg cccccagcc aggaagagat gaccaagaac    1080
caggtgagcc tgacctgcct ggtgaagggc ttctacccca gcgacattgc cgtcgagtgg    1140
gagagcaacg gccagcccga gaacaactac aagaccaccc cacctgtcct ggatagcgac    1200
ggcagcttct tcctgtacag caggctgacc gtggacaaga gcaggtggca ggagggcaac    1260
```

```
gtgttcagct gcagcgtgat gcacgaggcc ctgcacaacc actacaccca gaagagcctg    1320
agcctctccc tgggcaag                                                  1338

<210> SEQ ID NO 10
<211> LENGTH: 1338
<212> TYPE: DNA
<213> ORGANISM: Artificial Sequence
<220> FEATURE:
<223> OTHER INFORMATION: Polynucleotide encoding PanELR IgG4(PE)N297S
      Heavy Chain

<400> SEQUENCE: 10
caggtccagc tggtgcagag cggcgccgaa gtgaagaaac ccggcgctag cgtgaaggtg      60
agctgcaagg ccagcggcta caccttcacc aactactgga tcgtgtgggt caggcaggcc    120
cccggccagg gctggagtg gatgggcgac ctgtactcag gcggcggcta caccttctac     180
agcgagaact tcaagggcag ggtgaccatg accagggata ccagcaccag caccgtgtac    240
atggagctga gcagcctgag gagcgaggac actgccgtgt actattgcgc caggagcggc    300
tacgacagga cctggtttgc ccactgggga cagggcaccc tggtgaccgt cagctctgcc    360
tcaaccaagg gcccctcagt gttccctctg gccccctgta gcaggagcac cagcgagagc    420
accgccgccc tgggctgcct ggtgaaggac tacttccccg agcccgtgac cgtgagctgg    480
aatagcgggg ctctgactag cggagtgcac accttcccccg ccgtcctgca gtctagcggc    540
ctgtatagcc tgagcagcgt ggtcaccgtg ccaagcagca gcctgggcac caagacctac    600
acctgcaacg tggaccacaa gcccagcaac acaaaggtgg acaagagggt ggagtccaag    660
tacggccccc cctgccctcc ctgccccgca cccgagttcg agggcggccc ctccgtgttt    720
ctgttccccc ccaaacccaa ggacaccctg atgatcagca ggacccccga ggtgacttgc    780
gtggtggtgg acgtgagcca ggaggacccc gaggtgcagt tcaactggta cgtggacggc    840
gtggaggtgc acaacgccaa aaccaagccc agggaggagc agttcagcag cacctacagg    900
gtggtgagcg tgctgaccgt gctgcaccag gactggctca acggcaagga gtacaagtgc    960
aaggtgagca acaagggcct gcccagcagc atcgagaaga ccatcagcaa ggccaagggc   1020
cagcccagag agccacaggt gtacacactg ccccccagcc aggaggagat gaccaagaac   1080
caggtgagcc tgacctgcct ggtgaagggc ttctacccca gcgacatcgc cgtggagtgg   1140
gaaagcaacg gccagcccga gaacaactac aagaccaccc cccccgtgct cgatagcgac   1200
ggcagcttct tcctgtacag ccgcctgacc gtggacaaga gcaggtggca ggaaggcaac   1260
gtgttcagct gcagcgtgat gcacgaggcc ctccacaacc actacaccca gaagagcctg   1320
agcctgagcc tgggcaag                                                 1338
```

ANTIBODIES AGAINST THE CXC-ELR FAMILY OF CHEMOKINES

This application is a 371 of International Application No. PCT/EP2008/063289, filed Oct. 3, 2008, which claims the benefit of U.S. Provisional Application No. 60/977,841, filed Oct. 5, 2007, which are incorporated herein in their entirety. The specification includes no new matter.

FIELD OF THE INVENTION

The present invention relates to antibodies which have multiple specificities. In particular the antibodies of the present invention bind to (cross-react with) human IL-8, Gro-alpha, Gro-beta, Gro-gamma, GCP-2, and ENA-78. The present invention also concerns methods of treating diseases or disorders characterized by elevated or unbalanced level of one or more of human IL-8, Gro-alpha, Gro-beta, Gro-gamma, ENA-78 and GCP-2, particularly ulcerative colitis, Crohn's disease, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, respiratory syncytial virus, flu, Behcets disease, uveitis, periodontal disease particularly gingivitis, exacerbation of asthma and COPD, cystic fibrosis, acne, Bronchiolitis obliterans syndrome, diffuse panbronchiolitis, deep vein thrombosis, preeclampsia, vasculitis, familial Mediterranean fever, reperfusion injury, pain and/or endometriosis with said antibodies.

SUMMARY OF INVENTION

The present invention relates to improved antibodies or modification thereto to treat particularly ulcerative colitis, Crohn's disease, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, respiratory syncytial virus, flu, Behcets disease, uveitis, periodontal disease particularly gingivitis, exacerbation of asthma and COPD, cystic fibrosis, acne, Bronchiolitis obliterans syndrome, diffuse panbronchiolitis, deep vein thrombosis, preeclampsia, vasculitis, familial Mediterranean fever, reperfusion injury, pain and/or endometriosis with less inflammatory side effects.

BACKGROUND OF THE INVENTION

Figure 1:
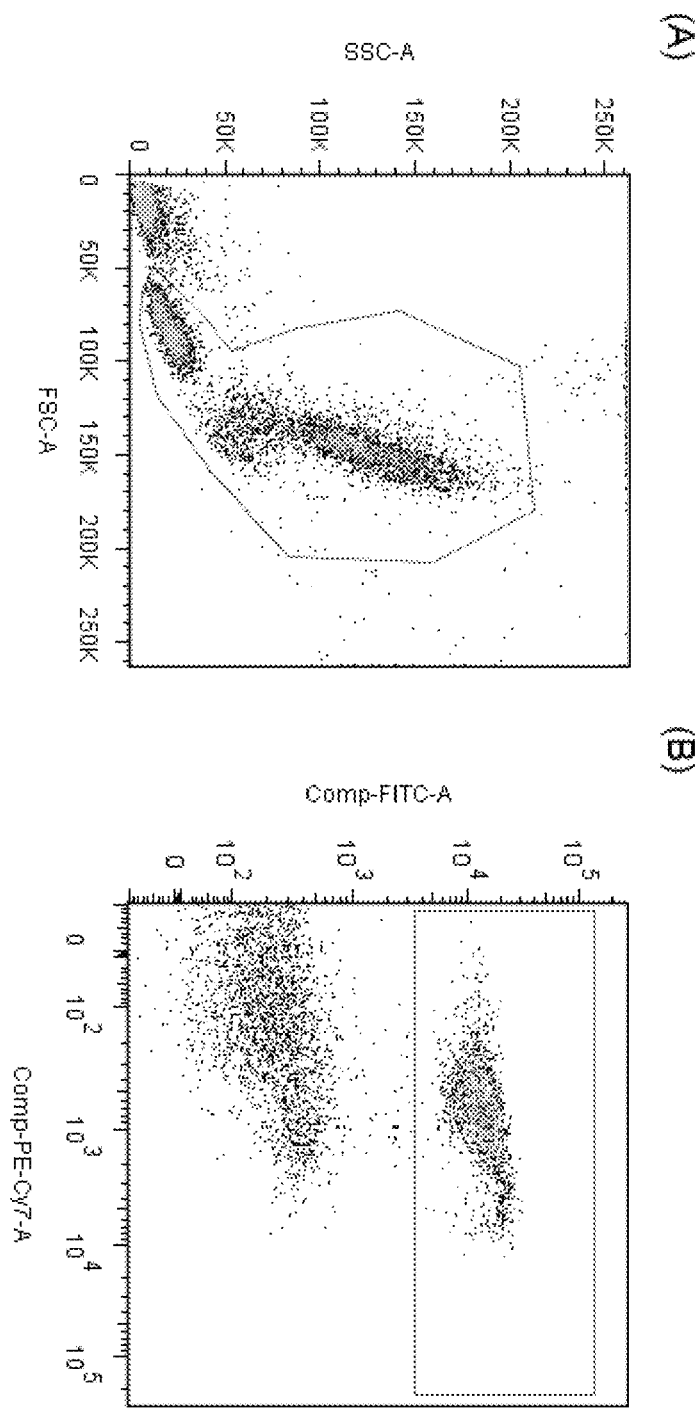
FIGS. 1A and B Measurement of neutrophil CD11b expression in stimulated human whole blood. Following incubation with PanELR antibody for 80 minutes (including 200 ng/ml IL-8 for the final 60 minutes, where indicated), heparinised whole blood from healthy volunteers was incubated with a fix/lyse solution (to lyse erythrocytes and fix leukocytes) and washed in phosphate-buffered saline. Leukocyte pellets were then stained with FITC-conjugated anti-CD16 and PE-Cy7-conjugated anti-CD11b and analysed by 2-colour flow cytometry. Leukocytes were identified by forward and side scatter profile (FIG. 1A); output was PE-Cy7 MFI in CD16(high) leukocytes (FIG. 1B). This was normalised to levels in unstimulated blood for graphical presentation.

Published data and reports indicate that the members of the ELRCXC subfamily of CXCL chemokines are elevated in a number of diseases. There are a total of 16 CXCL family members. The chemokines are reported to be up-regulated in a number of inflammatory diseases, including COPD, in which CXCL 1-3, 5 and 8, also known as Gro-alpha, -beta, -gamma (Haskill, S., et al. Proc. Nat. Acad. Sci. 1990: 87, 7732-7736), ENA-78 (Wang, D. and Richmond, A., Cytokine Reference. Oppenheim, J. J. and Feldman, M. ed., Academic Press, London, 1023-1027, Power, C. A. et al. Gene, 1994: 151, 333-334), and IL-8 (Lizasa, H. and Matsushima, K., Cytokine Reference. Oppenheim, J. J. and Feldman, M. ed., Academic Press, London, 1061-1067, Matsushima, K. et al., J. Exp. Med. 1988: 167, 1883-1893) respectively (Am. J. Respir. Crit. Care Med., 163: 349-355, 2001, Am. J. Respir. Crit. Care Med., 168: 968-975, 2003, Thorax, 57: 590-595, 2002). It has been postulated that prolonged and elevated expression of these chemokines could be involved in the development of diseases such as particularly ulcerative colitis, Crohn's disease, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, respiratory syncytial virus, flu, Behcets disease, uveitis, periodontal disease particularly gingivitis, exacerbation of asthma and COPD, cystic fibrosis, acne, Bronchiolitis obliterans syndrome, diffuse panbronchiolitis, deep vein thrombosis, preeclampsia, vasculitis, familial Mediterranean fever, reperfusion injury, pain and/or endometriosis. These CXC chemokines are known to stimulate neutrophil chemotaxis by engaging and activating the CXCR1 and CXCR2 receptors. Thus, the inhibition of these chemokines could prevent inflammatory cells from infiltrating the lung tissue and thus preventing tissue damage. The present invention is directed to inhibiting the activation of CXCR1 and CXCR2 receptors by using an antibody having the ability to bind to human IL-8, Gro-alpha, Gro-beta, Gro-gamma, GCP-2, and ENA-78.

DETAILED DESCRIPTION

Our published patent application WO2008/130969 teaches that antibody having heavy chain and light chain (SEQ ID NO: 1 and 2, respectively, referred to PanELR) decreases the neutrophil chemotaxis through inhibition of CXCR1 and CXCR2 receptor activation by neutralizing human IL-8, Gro-alpha, Gro-beta, Gro-gamma, gcp-2 and ENA-78.

PanELR is a humanized, IgG1 wild type antibody with potent neutralizing activity against the CXC-ELR family of chemokines (IL-8, gro-alpha, gro-beta, gro-gamma, ENA-78, and GCP-2). It specifically suppresses the infiltration of neutrophils in a number of animal models including the LPS inhaled model of lung inflammation and the cantharidin skin blister model: for example, at 10 mg/Kg i.v. suppresses over 90% of neutrophil, but not monocyte, infiltration demonstrating the specificity of this chemokine pathway.

In two GLP toxicology studies, run at doses of 3, 30, 100 and 300 mg/Kg with once weekly administration, the majority of animals in the high dose group (100-300 mg/Kg), and a minority of animals in the low (therapeutic) dose groups (3-10 mg/Kg), developed one to two skin lesions per animal. These lesions were marked by a monocytic or eosinophilic cell infiltration. To understand if the Fc-region of the wild type IgG1 antibody was playing a role in the inflammatory response, an IgG1 FcRn- and compliment-disabled antibody (PanELR Fc disabled, L248A/H250A, SEQ ID NO:2 and SEQ ID NO: 3 for light and heavy chains, respectively) was made and dosed at a single concentration of 300 mg/Kg once per week. These animals also developed skin lesions at approximately the same incidence rate as the animals dosed with the IgG1 wild type antibody, suggesting that Fc disablement of IgG1 wt antibodies may not be complete. In a separate observation, animals in the high dose IgG1 wt group also had an increased CD11b expression on neutrophils under non-stimulated conditions, leading to the hypothesis that PanELR may be stimulating neutrophils directly and that this could be part of the mechanism leading to toxicity.

Figure 2:
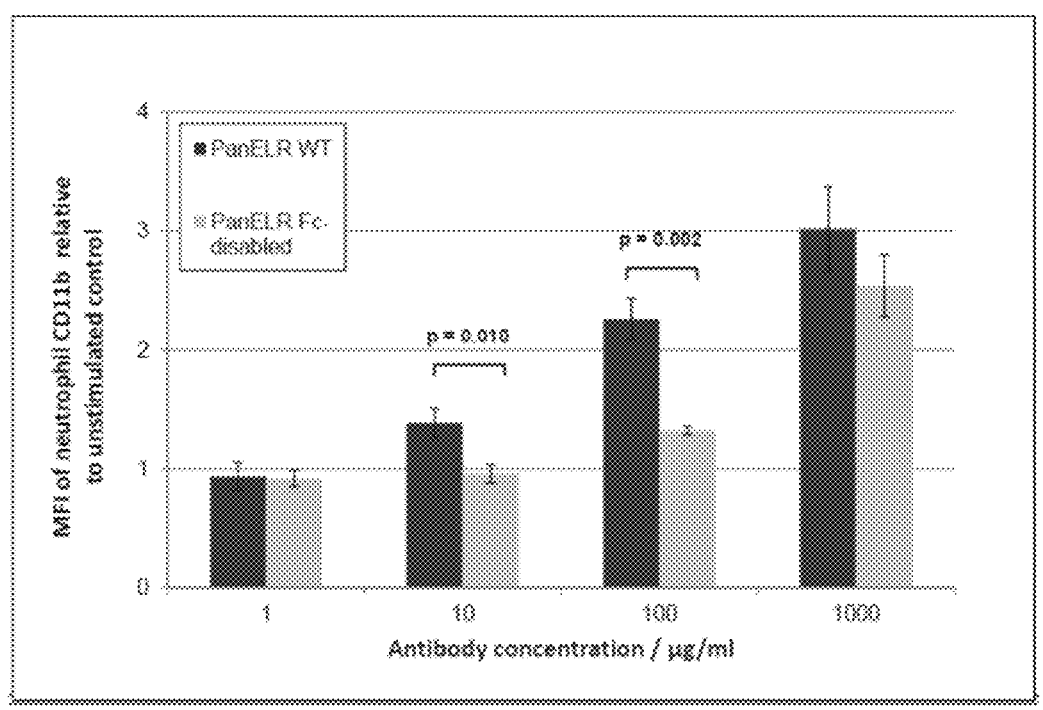
FIG. 2 Neutrophil CD11b Regulation in Whole Blood by PanELR [otherwise referred to as PanELR WT] and PanELR Fc-disabled antibodies.

To explore this potential, a number of experiments were conducted using whole human blood. As expected, PanELR (wild type) or the PanELR FcRn and compliment disabled antibody (PanELR Fc disabled) potently inhibited up-regulation of CD11b by exogenously added IL-8 (200 ug/ml). However, at higher concentrations, PanELR increased CD11b expression directly with or without the addition of IL-8. Interestingly, the PanELR Fc disabled also increased CD11b expression but not as potently as wt antibody except at concentrations above 1000 ug/ml (a concentration exceeded at the Cmaxin animals dosed with 300 mg/Kg of the antibody). (See FIG. 2) Fab fragments, derived from PanELR wt or PanELR Fc-disabled failed to promote the increase in CD11b at high concentrations, along with control Fc-wt and Fc disabled antibodies. These data suggest that there may be a direct cause-effect relationship between the Fc-region of PanELR and the increase in CD11b, which is not prevented by the alteration of IgG1 commonly used to disable IgG1 Fc function.

Figure 3:
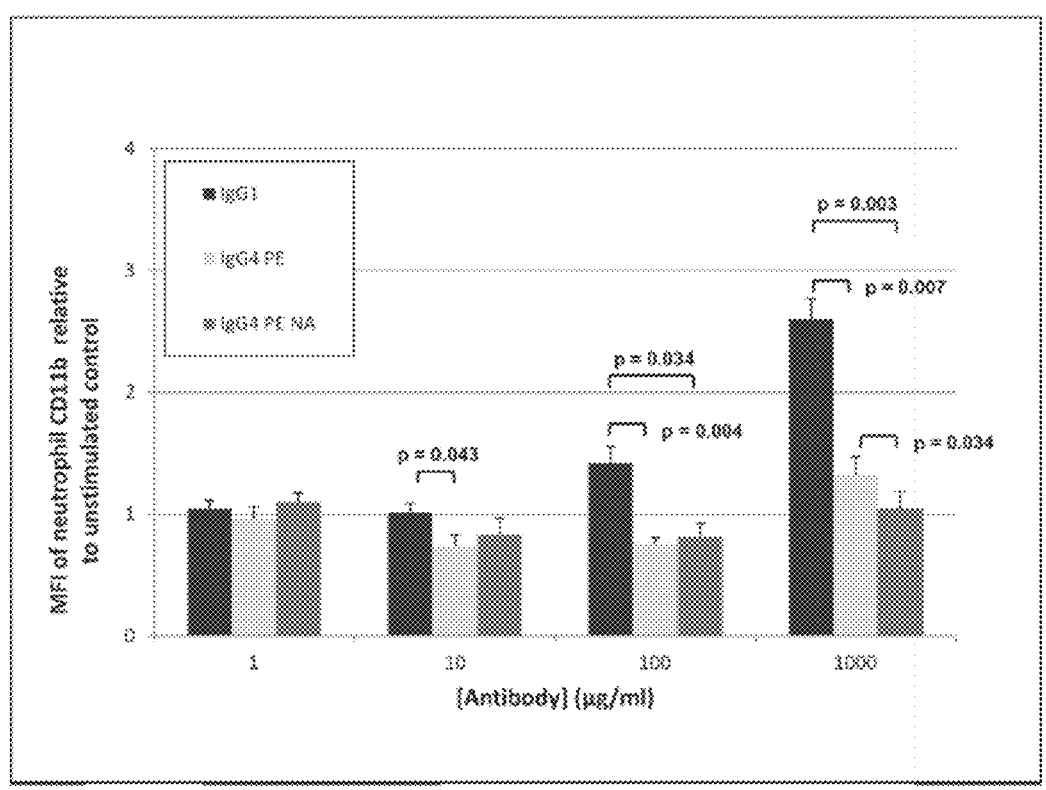
FIG. 3 Neutrophil CD11b Regulation by PanELR (IgG1), PanELR IgG4 (PE) [otherwise referred to as IgG4 PE] and PanELR IgG4 (PE) N297A [otherwise referred to as IgG4 PE NA].

In order to understand the role of the Fc portion of PanELR and its interaction with FcγR more fully, a stabilized and two aglycosylated forms of IgG4 were made: PanELR IgG4 (PE) antibody (having heavy and light chains with SEQ ID NO:4 and SEQ ID NO: 2 sequences, respectively); PanELR IgG4(PE)N297A antibody (having heavy and light chains with SEQ ID NO: 5 and SEQ ID NO: 2 sequences, respectively; and PanELR IgG4(PE)N297S antibody (having heavy and light chains with SEQ ID NO: 6 and SEQ ID NO:2 sequences, respectively) in which the CDR from PanELR was transposed onto an IgG4 backbone. Characterization of the IgG4 variants confirmed that they had the same binding and neutralizing characteristics as the IgG1 isotype. However, in contrast to IgG1 isotypes, exposure of whole blood to some of these IgG4 variants failed to show an increase or had minimal expression in CD11b at concentrations up to 1000 ug/ml, (See FIG. 3) suggesting that IgG4 variants may have a lower interaction with FcγR than either IgG1 or IgG1-Fc-disabled aversions.

In order to characterize the interactions of Pan-ELR IgG variants with compliment, a C1q BiaCore binding assay was established that reveled greater than 65% reduction in IgG4 (PE) variant of Pan-ELR binding to C1q. This demonstrates that IgG4(PE) has less binding and thus potential, to activate compliment than either IgG1 wild type or Fc disabled antibodies and is an important consideration when reducing the inflammatory potential of an antibody.

This set of experiments reveals an unexpected finding and shows for the first time that disablement of IgG1 antibody by the introduction of a double alanine mutation does not result in the complet emimination of Fc-gamma receptor interaction or C1q binding and in addition demonstrates the superior advantage of an IgG4 antibody over IgG1 Fc-disabled antibody where FcγR and compliment interactions may be playing an inflammatory role.

Thus in one embodiment the present invention relates to an isolated antibody comprising heavy and light chains comprising polypeptides of SEQ ID NO:4 and SEQ ID NO:2, respectively; or an isolated antibody comprising heavy and light chains comprising polypeptides of SEQ ID NO:5 and SEQ ID NO:2, respectively.

In another aspect, the invention relates to a method of preventing, treating or ameliorating in a human particularly ulcerative colitis, Crohn's disease, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, respiratory syncytial virus, flu, Behcets disease, uveitis, periodontal disease particularly gingivitis, exacerbation of asthma and COPD, cystic fibrosis, acne, Bronchiolitis obliterans syndrome, diffuse panbronchiolitis, deep vein thrombosis, preeclampsia, vasculitis, familial Mediterranean fever, reperfusion injury, pain and/or endometriosis comprising administering an effective amount of an isolated antibody comprising heavy and light chains comprising polypeptides of SEQ ID NO:4 and SEQ ID NO:2, respectively; or an isolated antibody comprising heavy and light chains comprising polypeptides of SEQ ID NO:5 and SEQ ID NO:2, respectively.

In one embodiment, the present invention relates to a recombinant host cell which produces an isolated antibody comprising heavy and light chains comprising polypeptides of SEQ ID NO:4 and SEQ ID NO:2, respectively; or an isolated antibody comprising heavy and light chains comprising polypeptides of SEQ ID NO:5 and SEQ ID NO:2, respectively.

As used herein "antibodies" include various modified forms. Modifications include glycosylation variants of the antibodies. Glycosylation of antibodies at conserved positions in their constant regions is known to have a profound effect on antibody function, particularly effector functioning such as those described above, see for example, Boyd et al. (1996) Mol. Immunol. 32: 1311-1318. Glycosylation variants of the antibodies or antibody fragments thereof wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al. (2001) Biochemistry 40: 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al. (2004) Science 303: 371: Sears et al. (2001) Science 291: 2344; Wacker et al. (2002) Science 298: 1790; Davis et al. (2002) Chem. Rev. 102: 579; Hang et al. (2001) Acc. Chem. Res 34: 727. The antibodies (for example of the IgG isotype, e.g. IgG1) as herein described may comprise a defined number (e.g. 7 or less, for example 5 or less, such as two or a single) of glycoform(s).

The antibodies of the invention may be coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis et al. (2000) Int. J. Pharmaceut. 198: 83-95.

Production Methods

The antibodies of the present invention may be produced in transgenic organisms such as goats (see Pollock et al. (1999) J. Immunol. Methods 231: 147-157), chickens (see Morrow (2000) Genet. Eng. News 20:1-55, mice (see Pollock et al.) or plants (see Doran (2000) Curr. Opinion Biotechnol. 11: 199-204; Ma (1998) Nat. Med. 4: 601-606; Baez et al. (2000) BioPharm 13: 50-54; Stoger et al. (2000) Plant Mol. Biol. 42: 583-590).

The antibodies of the present invention may also be produced by chemical synthesis. However, they are typically produced using recombinant cell culturing technology well known to those skilled in the art. A polynucleotide encoding the antibody of the present invention is isolated and inserted into a replicable vector such as a plasmid for further cloning (amplification) or expression. One expression system is a glutamate synthetase system (such as sold by Lonza Biologics), particularly where the host cell is CHO or NS0. Polynucleotide encoding the antibody is readily isolated and sequenced using conventional procedures (e.g. oligonucleotide probes). Vectors that may be used include plasmid, virus, phage, transposons, minichromosomes of which plasmids are typically used. Generally such vectors further include a signal sequence, origin of replication, one or more marker genes, an enhancer element, a promoter and transcription termination sequences operably linked to the antibody polynucleotide so as to facilitate expression. Polynucleotide encoding the light and heavy chains may be inserted into separate vectors and introduced (for example by transformation, transfection, electroporation or transduction) into the same host cell concurrently or sequentially or, if desired, both the heavy chain and light chain can be inserted into the same vector prior to said introduction.

In one embodiment, the present invention relates to an expression vector comprising polynucleotide which encode heavy chain comprising polypeptide of SEQ ID NO:4 or SEQ ID NO:5; or light chain comprising polypeptide of SEQ ID NO:2.

Codon optimisation may be used with the intent that the total level of protein produced by the host cell is greater when transfected with the codon-optimised gene in comparison with the level when transfected with the sequence. Several methods have been published (Nakamura et al. (1996) Nucleic Acids Research 24: 214-215; WO98/34640; WO97/11086). Due to the redundancy of the genetic code, alternative polynucleotides to those disclosed herein (particularly those codon optimised for expression in a given host cell) may also encode the antibodies described herein. The codon usage of the antibody of this invention therefore can be modified to accommodate codon bias of the host cell such to augment transcript and/or product yield (e.g. Hoekema et al Mol Cell Biol 1987 7(8): 2914-24). The choice of codons may be based upon suitable compatibility with the host cell used for expression.

Thus in another aspect, the present invention relates to a polynucleotide comprising polynucleotide having at least 90, 95, 98, or 99% or 100% identical to polynucleotide sequence of SEQ ID NO: 7, 8, 9, or 10.

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

Signal Sequences

Antibodies may be produced as a fusion protein with a heterologous signal sequence having a specific cleavage site at the N-terminus of the mature protein. The signal sequence should be recognised and processed by the host cell. For prokaryotic host cells, the signal sequence may be for example an alkaline phosphatase, penicillinase, or heat stable enterotoxin II leaders. For yeast secretion the signal sequences may be for example a yeast invertase leader, α factor leader or acid phosphatase leaders see e.g. WO90/13646. In mammalian cell systems, viral secretory leaders such as herpes simplex gD signal and a native immunoglobulin signal sequence may be suitable. Typically the signal sequence is ligated in reading frame to DNA encoding the antibody.

Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

Selection Marker

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media or (c) combinations of both. The selection scheme may involve arresting growth of the host cell. Cells, which have been successfully transformed with the genes encoding the antibody of the invention, survive due to e.g. drug resistance conferred by the co-delivered selection marker. One example is the DHFR selection marker wherein transformants are cultured in the presence of methotrexate. Cells can be cultured in the presence of increasing amounts of methotrexate to amplify the copy number of the exogenous gene of interest. CHO cells are a particularly useful cell line for the DHFR selection. A further example is the glutamate synthetase expression system (Lonza Biologics). An example of a selection gene for use in yeast is the trp1 gene, see Stinchcomb et al. (1979) Nature 282: 38.

Promoters

Suitable promoters for expressing antibody of the present invention are operably linked to DNA/polynucleotide encoding the antibody. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression. A first plasmid may comprise a RSV and/or SV40 and/or CMV promoter, DNA encoding light chain variable region (VL), κC region together with neomycin and ampicillin resistance selection markers and a second plasmid comprising a RSV or SV40 promoter, DNA encoding the heavy chain variable region (VH), DNA encoding the γ1 constant region, DHFR and ampicillin resistance markers.

Enhancer Element

Where appropriate, e.g. for expression in higher eukaryotes, an enhancer element operably linked to the promoter element in a vector may be used. Mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer may be located on the vector at a site upstream to the promoter. Alternatively, the enhancer may be located elsewhere, for example within the untranslated region or downstream of the polyadenylation signal. The choice and positioning of enhancer may be based upon suitable compatibility with the host cell used for expression.

Polyadenylation/Termination

In eukaryotic systems, polyadenylation signals are operably linked to DNA/polynucleotide encoding the antibody. Such signals are typically placed 3' of the open reading frame. In mammalian systems, non-limiting examples include signals derived from growth hormones, elongation factor-1 alpha and viral (e.g. SV40) genes or retroviral long terminal repeats. In yeast systems non-limiting examples of polyadenylation/termination signals include those derived from the phosphoglycerate kinase (PGK) and the alcohol dehydrogenase 1 (ADH) genes. In prokaryotic systems, polyadenylation signals are typically not required and it is instead usual to employ shorter and more defined terminator sequences. The choice of polyadenylation/termination sequences may be based upon suitable compatibility with the host cell used for expression.

Other Methods/Elements for Enhanced Yields

In addition to the above, other features that can be employed to enhance yields include chromatin remodelling elements, introns and host-cell specific codon modification.

Host Cells

Suitable host cells for cloning or expressing vectors encoding the antibody are prokaroytic, yeast or higher eukaryotic cells. Suitable prokaryotic cells include eubacteria e.g. enterobacteriaceae such as *Escherichia* e.g. *E. coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g. ATCC 16,045; 12,424; 24178; 56,500), *yarrowia* (EP402, 226), *Pichia pastoris* (EP 183 070, see also Peng et al. (2004) J. Biotechnol. 108: 185-192), *Candida, Trichoderma reesia* (EP 244 234), Penicillin, *Tolypocladium* and *Aspergillus* hosts such as *A. nidulans* and *A. niger* are also contemplated.

Higher eukaryotic host cells include mammalian cells such as COS-1 (ATCC No. CRL 1650) COS-7 (ATCC CRL 1651), human embryonic kidney line 293, baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al. (1986) Somatic Cell Mol. Genet. 12: 555-556), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Such host cells may also be further engineered or adapted to modify quality, function and/or yield of an antibody. Non-limiting examples include expression of specific modifying (e.g. glycosylation) enzymes and protein folding chaperones.

Cell Culturing Methods

Host cells transformed with vectors encoding an antibody may be cultured by any method known to those skilled in the art. Host cells may be cultured in spinner flasks, roller bottles or hollow fibre systems but for large scale production that stirred tank reactors are used particularly for suspension cultures. The stirred tankers may be adapted for aeration using e.g. spargers, baffles or low shear impellers. For bubble columns and airlift reactors direct aeration with air or oxygen bubbles maybe used. Where the host cells are cultured in a serum free culture media, the media is supplemented with a cell protective agent such as pluronic F-68 to help prevent cell damage as a result of the aeration process. Depending on the host cell characteristics, either microcarriers maybe used as growth substrates for anchorage dependent cell lines or the cells may be adapted to suspension culture (which is typical). The culturing of host cells, particularly invertebrate host cells may utilise a variety of operational modes such as fed-batch, repeated batch processing (see Drapeau et al. (1994) Cytotechnology 15: 103-109), extended batch process or perfusion culture. Although recombinantly transformed mammalian host cells may be cultured in serum-containing media such as fetal calf serum (FCS), such host cells may be cultured in synthetic serum-free media such as disclosed in Keen et al. (1995) Cytotechnology 17: 153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg et al. (1995) in Animal Cell Technology: Developments towards the 21st century (Beuvery et al. eds, 619-623, Kluwer Academic publishers).

The antibody secreted into the media may be recovered and purified using a variety of techniques to provide a degree of purification suitable for the intended use. For example the use of the antibody for the treatment of human patients typically mandates at least 95% purity, more typically 98% or 99% or greater purity (compared to the crude culture medium). Cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. The antibodies, following various clarification steps, can be captured using Protein A or G affinity chromatography. Further chromatography steps can follow such as ion exchange and/or HA chromatography, anion or cation exchange, size exclusion chromatography and ammonium sulphate precipitation. Various virus removal steps may also be employed (e.g. nanofiltration using e.g. a DV-20 filter). Following these various steps, a purified (for example a monoclonal) preparation comprising at least 75 mg/ml or greater, or 100 mg/ml or greater, of the antibody is provided. Such preparations are substantially free of aggregated forms of antibodies.

Bacterial systems may be used for the expression of antibodies. Such fragments can be localised intracellularly, within the periplasm or secreted extracellularly. Insoluble proteins can be extracted and refolded to form active proteins according to methods known to those skilled in the art, see Sanchez et al. (1999) J. Biotechnol. 72: 13-20; and Cupit et al. (1999) Lett Appl Microbiol 29: 273-277.

The skilled person will appreciate that, upon production of the antibody, in particular depending on the cell line used and particular amino acid sequence of the antibody, post-translational modifications may occur. For example, this may include the cleavage of certain leader sequences, the addition of various sugar moieties in various glycosylation patterns, deamidation, oxidation, disulfide bond scrambling, isomerisation, C-terminal lysine clipping, and N-terminal glutamine cyclisation. The present invention encompasses the use of antibodies which have been subjected to, or have undergone, one or more post-translational modifications.

Deamidation is an enzymatic reaction primarily converting asparagine (N) to iso-aspartic acid and aspartic acid (D) at approximately 3:1 ratio. To a much lesser degree, deamidation can occur with glutamine residues in a similar manner. Deamidation in a CDR results in a change in charge of the molecule, but typically does not result in a change in antigen binding, nor does it impact on PK/PD.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but occasionally can occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

Isomerization typically occurs during production, purification, and storage (at acidic pH) and usually occurs when aspartic acid is converted to isoaspartic acid through a chemical process.

N-terminal glutamine in the heavy chain and/or light chain is likely to form pyroglutamate (pGlu). Most pGlu formation happens in the production bioreactor, but it can be formed non-enzymatically, depending on pH and temperature of processing and storage conditions. pGlu formation is considered as one of the principal degradation pathways for recombinant mAbs.

C-terminal lysine clipping is an enzymatic reaction catalyzed by carboxypeptidases, and is commonly observed in recombinant mAbs. Variants of this process include removal of lysine from one or both heavy chains. Lysine clipping does not appear to impact bioactivity and has no effect on mAb effector function.

Pharmaceutical Compositions

Purified preparations of an antibody or fragments thereof of the present invention as described herein may be incorporated into pharmaceutical compositions for use in the treatment of the human diseases, disorders and conditions described herein. The terms diseases, disorders and conditions are used interchangeably. The pharmaceutical preparation may comprise an antibody in combination with a pharmaceutically acceptable carrier. The antibody may be administered alone, or as part of a pharmaceutical composition.

Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilised carriers such as saline, Ringers solution or dextrose solution, optionally buffered with suitable buffers to a pH within a range of 5 to 8.

Pharmaceutical compositions may be administered by injection or continuous infusion (e.g. intravenous, intraperitoneal, intradermal, subcutaneous, intramuscular or intraportal). Such compositions are suitably free of visible particulate matter. Pharmaceutical compositions may also be administered orally, specifically those containing CPHPC.

Pharmaceutical compositions may comprise between 1 mg to 10 g of the antibody, for example between 5 mg and 1 g of antibody. Alternatively, the composition may comprise between 5 mg and 500 mg, for example between 5 mg and 50 mg.

Methods for the preparation of such pharmaceutical compositions are well known to those skilled in the art. Pharmaceutical compositions may comprise between 1 mg to 10 g of antibody in unit dosage form, optionally together with instructions for use. Pharmaceutical compositions may be lyophilised (freeze dried) for reconstitution prior to administration according to methods well known or apparent to those skilled in the art. Where antibodies have an IgG1 isotype, a chelator of copper, such as citrate (e.g. sodium citrate) or EDTA or histidine, may be added to the pharmaceutical composition to reduce the degree of copper-mediated degradation of antibodies of this isotype, see EP0612251. Pharmaceutical compositions may also comprise a solubiliser such as arginine base, a detergent/antiaggregation agent such as polysorbate 80, and an inert gas such as nitrogen to replace vial headspace oxygen.

Effective doses and treatment regimes for administering the antibody are generally determined empirically and may be dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York.

The dosage of antibody administered to a subject is generally between 1 µg/kg to 150 mg/kg, between 0.1 mg/kg and 100 mg/kg, between 0.5 mg/kg and 50 mg/kg, between 1 and 25 mg/kg or between 1 and 10 mg/kg of the subject's body weight. For example, the dose may be 10 mg/kg, 30 mg/kg, or 60 mg/kg. The antibody may be administered parenterally, for example subcutaneously, intravenously or intramuscularly.

If desired, the effective daily dose of a therapeutic composition may be administered as two, three, four, five, six or more sub-doses administered separately at appropriate intervals throughout the day, optionally, in unit dosage forms.

The antibody may be administered in a single large dose or in smaller repeated doses.

The administration of a dose may be by slow continuous infusion over a period of from 2 to 24 hours, such as from 2 to 12 hours, or from 2 to 6 hours. This may result in reduced toxic side effects.

The administration of a dose may be repeated one or more times as necessary, for example, three times daily, once every day, once every 2 days, once a week, once a fortnight, once a month, once every 3 months, once every 6 months, or once every 12 months. The antibody may be administered by maintenance therapy, for example once a week for a period of 6 months or more. The antibody may be administered by intermittent therapy, for example for a period of 3 to 6 months and then no dose for 3 to 6 months, followed by administration of antibody again for 3 to 6 months, and so on in a cycle.

For example, the dose may be administered subcutaneously, once every 14 or 28 days in the form of multiple sub-doses on each day of administration.

Accordingly, the administration may use a pre-determined or routine schedule for administration, thereby resulting in a predetermined designated period of time between dose administrations. The schedule may encompass periods of time which are identical or which differ in length, as long as the schedule is predetermined. Any particular combination would be covered by the schedule as long as it is determined ahead of time that the appropriate schedule involves administration on a certain day.

The pharmaceutical composition may comprise a kit of parts of the antibody together with other medicaments, optionally with instructions for use. For convenience, the kit may comprise the reagents in predetermined amounts with instructions for use.

Treatment can be therapeutic, prophylactic or preventative. The subject will be one who is in need thereof. Those in need of treatment may include individuals already suffering from a particular medical disease in addition to those who may develop the disease in the future.

The antibody described herein may also be used in methods of therapy. The term "therapy" encompasses alleviation, reduction, or prevention of at least one aspect or symptom of a disease. For example, the antibody described herein may be used to ameliorate or reduce one or more aspects or symptoms of a disease described herein.

The antibody described herein is used in an effective amount for therapeutic, prophylactic or preventative treatment. A therapeutically effective amount of the antibody described herein is an amount effective to ameliorate or reduce one or more aspects or symptoms of the disease. The antibody described herein may also be used to treat, prevent, or cure the disease described herein.

The antibody described herein need not affect a complete cure, or eradicate every symptom or manifestation of the disease to constitute a viable therapeutic treatment. As is recognised in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

Diagnostic Methods of Use

The antibodies described herein may be provided in a diagnostic kit comprising one or more antibodies, a detectable label, and instructions for use of the kit. For convenience, the kit may comprise the reagents in predetermined amounts with instructions for use.

In one embodiment the present invention relates to a process for producing an antibody in a single host cell, comprising the steps of:
 (i) transforming said single host cell with a first DNA sequence encoding a heavy chain comprising polypeptide of SEQ ID NO: 4 or 5; and a second DNA sequence encoding a light chain comprising a polypeptide of SEQ ID NO: 2; and
 (ii) expressing said first DNA sequence and said second DNA sequence so that said antibody heavy and light chains are produced in said transformed single host cell.

Furthermore, this process can be carried out such that said first and second DNA sequences are present in different vectors or said first and second DNA sequences are present in a single vector.

EXPERIMENTAL DETAILS

Example 1

FIG. 1

Blood from healthy human subjects was collected (with informed consent) into sodium heparin tubes. For each data point, 80 µl of whole blood was pipetted into a polypropylene tube containing 10 µl PanELR antibody at the appropriate concentration (10× the final concentration), mixed thoroughly and incubated for 20 minutes at 37° C. in a humidified incubator. A further 10 µl of vehicle (PBS) was added to each tube and, after thorough mixing, tubes were returned to the incubator for a further 60 minutes. Reactions were stopped by addition of 1 ml of fixation/lysis buffer; after incubation for a further 10 minutes at 37° C. leukocytes were harvested by centrifugation (500×g for 10 minutes), washed with 2 ml PBS, stained for 45 minutes with antibodies against human CD16 (FITC-labelled) and CD11b (PE-Cy7 labelled), washed with a further 2 ml of PBS and finally suspended in 300 µl of PBS before analysis on a BD FACSCANTO II flow cytometer. For each data point, 20,000-50,000 total events were captured. Neutrophil CD11b expression was quantified as PE-Cy7 mean fluorescent intensity in leukocytes (gated on forward scatter/side scatter profile—FIG. 1A) expressing high levels of CD16 (gated using the FITC channel—FIG. 1B). All data were expressed as fold-increase relative to baseline (i.e. neutrophil CD11b MFI in whole blood incubated with vehicle only for 20+60 minutes) for graphical presentation (as in FIGS. 2 and 3)

Example 2

FIG. 2

Whole blood was treated for 80 minutes with the indicated concentration of antibody. Neutrophil CD11b was assessed by flow cytometry as fold change in PE-Cy7 MFI over baseline (blood treated with vehicle for 80 minutes) in neutrophils (gated for high CD16 expression), following fixation/lysis of whole blood and staining of leukocytes with FITC-labelled anti-CD16 and PE-Cy7 labelled anti-CD11b. Bars show mean+/−SEM (n=6); probabilities by paired T test Example 3

FIG. 3

Whole blood was treated for 80 minutes with the indicated concentration of antibody. Neutrophil CD11b was assessed by flow cytometry as fold change in PE-Cy7 MFI over baseline (blood treated with vehicle for 80 minutes) in neutrophils (gated for high CD16 expression), following fixation/lysis of whole blood and staining of leukocytes with FITC-labelled anti-CD16 and PE-Cy7 labelled anti-CD11b. Bars show mean+/−SEM (n=6); probabilities by paired T test

```
PanELR Heavy Chain
                                                             (SEQ ID NO: 1)
QVQLVQSGAEVKKPGASVKVSCKASGYTFTNYWIVWVRQAPGQGLEWMGDLYSGGGYTFYSENFKGRVTMTR

DTSTSTVYMELSSLRSEDTAVYYCARSGYDRTWFAHWGQGTLVTVSSASTKGPSVFPLAPSSKSTSGGTAAL

GCLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLTVDKSRWQQGNVFSCSVMHE

ALHNHYTQKSLSLSPGK

PanELR Light Chain
                                                             (SEQ ID NO: 2)
DIQMTQSPSSLSASVGDRVTITCQASQDIESYLSWYQQKPGKAPKLLIYYATRLADGVPSRFSGSGSGQDYT

LTISSLQPEDFATYYCLQHGESPPTFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKSFNRGEC

PanELR Fc Disabled Heavy Chain
                                                             (SEQ ID NO: 3)
QVQLVQSGAEVKKPGASVKVSCKASGYTFTNYWIVWVRQAPGQGLEWMGDLYSGGGYTFYSENFKGRVTMTR

DTSTSTVYMELSSLRSEDTAVYYCARSGYDRTWFAHWGQGTLVTVSSASTKGPSVFPLAPSSKSTSGGTAAL

GCLVKDYFPEPVTVSWNSGALTSGVHTFPAVLQSSGLYSLSSVVTVPSSSLGTQTYICNVNHKPSNTKVDKK

VEPKSCDKTHTCPPCPAPELAGAPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLTVDKSRWQQGNVFSCSVMHE

ALHNHYTQKSLSLSPGK.

PanELR IgG4 (PE) Heavy Chain
                                                             (SEQ ID NO: 4)
QVQLVQSGAEVKKPGASVKVSCKASGYTFTNYWIVWVRQAPGQGLEWMGDLYSGGGYTFYSENFKGRVTMTR

DTSTSTVYMELSSLRSEDTAVYYCARSGYDRTWFAHWGQGTLVTVSSASTKGPSVFPLAPCSRSTSESTAAL

GCLVKDYFPEPVTVSWNSGALTSGVHTFPAVLQSSGLYSLSSVVTVPSSSLGTKTYTCNVDHKPSNTKVDKR

VESKYGPPCPPCPAPEFEGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALH

NHYTQKSLSLSLGK
```

PanELR IgG4(PE)N297A Heavy Chain
(SEQ ID NO: 5)
QVQLVQSGAEVKKPGASVKVSCKASGYTFTNYWIVWVRQAPGQGLEWMGDLYSGGGYTFYSENFKGRVTMTR

DTSTSTVYMELSSLRSEDTAVYYCARSGYDRTWFAHWGQGTLVTVSSASTKGPSVFPLAPCSRSTSESTAAL

GCLVKDYFPEPVTVSWNSGALTSGVHTFPAVLQSSGLYSLSSVVTVPSSSLGTKTYTCNVDHKPSNTKVDKR

VESKYGPPCPPCPAPEFEGGPSVFLFPPKPKDTLMISRTPEVTCVVVDVSQEDPEVQFNWYVDGVEVHNAKT

KPREEQFASTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALH

NHYTQKSLSLSLGK

PanELR IgG4(PE)N297S Heavy Chain
(SEQ ID NO: 6)
QVQLVQSGAEVKKPGASVKVSCKASGYTFTNYWIVWVRQAPGQGLEWMGDLYSGGGYTFYSENFKGRVTMTR

DTSTSTVYMELSSLRSEDTAVYYCARSGYDRTWFAHWGQGTLVTVSSASTKGPSVFPLAPCSRSTSESTAAL

GCLVKDYFPEPVTVSWNSGALTSGVHTFPAVLQSSGLYSLSSVVTVPSSSLGTKTYTCNVDHKPSNTKVDKR

VESKYGPPCPPCPAPEFEGGPSVFLFPPKPKDTLMISRTPEVTCVVVDVSQEDPEVQFNWYVDGVEVHNAKT

KPREEQFSSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALH

NHYTQKSLSLSLGK

Polynucleotide encoding PanELR Fc disabled Heavy Chain
(SEQ ID NO: 7)
CAGGT CCAGC TGGTG CAGAG CGGCG CCGAG GTGAA GAAGC CCGGC GCCAG

CGTGA AGGTG AGCTG CAAGG CCAGC GGCTA CACCT TCACC AACTA CTGGA

TCGTG TGGGT GAGGC AGGCC CCCGG CCAGG GCCTG GAGTG GATGG GAGAC

CTGTA CAGCG GCGGC GGCTA CACCT TCTAC AGCGA GAACT TCAAG GGCAG

GGTGA CTATG ACCCG GGACA CCAGC ACCTC TACCG TGTAC ATGGA GCTGA

GCAGC CTGAG GTCAG AGGAT ACCGC CGTGT ACTAC TGTGC CAGGA GCGGC

TACGA CAGGA CTTGG TTCGC CCACT GGGGC CAGGG CACCC TGGTG ACCGT

CAGCT CAGCC AGCAC CAAAG CCCCC AGCGT GTTCC CCCTG GCTCC CAGCA

GCAAA GCACA GCGGC ACCGC CGCCC TGGGC TGCCT GGTCA AGGAC

TACTT CCCCG AGCCC GTGAC CGTGA GCTGG AATAG CGGCG CCCTG ACAAG

CGGCG TGCAC ACCTT CCCCG CCGTG CTCCA GTCTA CGGCC TGTA CAGCC

TGAGC AGCGT GGTGA CAGTG CCTAG CAGCA GCCTG GCCAC CCAGA CCTAC

ATCTG CAACG TGAAC CACAA GCCCA GCAAC ACCAA GGTGG ACAAG AAGGT

CGAAC CCAAG AGCTG CGACA AGACC CACAC CTGCC CACCT TGCCC CGCAC

CCGAA CTCGC CGGCG CCCCT AGCGT CTTCC TGTTC CCACC CAAGC CCAAG

GACAC CCTGA TGATC AGCAG GACCC CCGAG GTGAC CTGCG TGGTG GTGGA

CGTGA GCCAC GAGGA CCCCG AGGTG AAGTT CAACT GGTAC GTGGA CGGCG

TGGAG GTGCA CAACG CCAAG ACCAA GCCCA GGGAG GAGCA GTACA ACTCC

ACCTA CAGGG TGGTG AGCGT GCTGA CCGTG CTGCA CCAGG ACTGG CTGAA

CGGGA AGGAG TACAA GTGCA AGGTG AGCAA CAAGG CCCTG CCCGC CCCCA

TCGAG AAAAC CATCA GCAAG GCCAA GGCCC AGCCC AGAGA GCCTC AGGTG

TATAC CCTGC CCCCA AGCAG GGACG AGCTG ACCAA GAACC AGGTG AGCCT

GACCT GCCTG GTGAA GGGCT TCTAT CCCAG CGACA TTGCC GTGGA GTGGG

AGAGC AACGG ACAGC CCGAG AACAA CTACA AGACC ACCCC CCCCG TCCTG

```
GATAG CGACG GCAGC TTCTT CCTGT ACAGC AAGCT GACCG TGGAC AAGAG
CAGGT GGCAG CAGGG CAACG TGTTT AGCTG TAGCG TGATG CACGA GGCCC
TCCAC AACCA CTACA CCCAG AAGTC CCTGA GCCTG AGCCC CGGCA AG
```

Polynucleotide encoding PanELR IgG4 (PE) Heavy Chain (SEQ ID NO: 8)

```
CAGGT GCAGC TGGTG CAGAG CGGCG CAGAG GTGAA GAAAC CCGGC GCTTC
CGTGA AGGTG AGCTG TAAGG CCAGC GGCTA CACCT TCACC AACTA CTGGA
TCGTG TGGGT GAGGC AGGCC CCCGG CCAGG CCTGG AGTGG ATGGG CGAC
CTGTA CAGCG GGGGC GGCTA CACCT TCTAC AGCGA GAACT TCAAG GGCAG
GGTGA CCATG ACTAG GGACA CCTCC ACCAG CACCG TGTAC ATGGA GCTGT
CCAGC CTGAG GAGCG AGGAC ACCGC CGTGT ATTAC TGCGC CCGGA GCGGC
TACGA TAGGA CTTGG TTCGC CCACT GGGGC CAGGG CACCC TGGTC ACCGT
GAGCA GCGCT AGCAC CAAAG GCCCT AGCGT GTTCC CCCTG GCCCC CTGCT
CTAGG AGCAC ATCTG AGAGC ACAGC CGCCC TGGGC TGCCT GGTGA AGGAC
TACTT CCCCG AGCCC GTGAC CGTGT CTTGG AACAG CGGAG CACTC ACCAG
CGGCG TGCAC ACCTT CCCTG CCGTG CTGCA GAGCA GCGGC CTGTA CAGCC
TGAGC AGCGT GGTGA CCGTG CCAAG CAGCA GCCTG GGCAC CAAGA CCTAC
ACCTG CAACG TGGAC CACAA GCCCA GCAAC ACCAA GGTGG ACAAG AGGGT
GGAGA GCAAA TACGG ACCCC CCTGC CCCCC CTGCC CCGCC CCCGA GTTTG
AAGGA GGCCC CAGCG TGTTC CTGTT CCCCC CAAGC CCAA GGACA CCCTG
ATGAT CAGCA GGACC CCCGA AGTGA CCTGC GTGGT GGTGG ACGTG AGCCA
GGAGG ACCCC GAAGT GCAGT TCAAC TGGTA CGTGG ACGGC GTCGA GGTGC
ACAAC GCCAA GACCA AGCCC AGAGA GGAGC AGTTC AACAG CACCT ACAGG
GTGGT GTCAG TGCTC ACCGT GCTGC ATCAG GACTG GCTGA ACGGC AAGGA
GTACA AGTGC AAGGT CAGCA ACAAG GGCCT GCCCA GCAGC ATCGA GAAGA
CCATC AGCAA GGCCA AGGGC CAGCC AAGGG AGCCC CAGGT CTATA CCCTG
CCCCC CAGCC AGGAG GAGAT GACCA AGAAC CAGGT GTCCC TGACC TGCCT
GGTCA AGGGC TTCTA CCCCA GCGAC ATTGC CGTGG AGTGG GAGAG CAACG
GCCAG CCCGA GAACA ACTAC AAGAC CACCC CCCCC GTGCT GGATA GCGAC
GGGAG CTTCT TCCTG TACAG CAGGC TGACC GTGGA CAAAA GCAGG TGGCA
GGAGG GCAAC GTGTT CAGCT GCTCC GTGAT GCACG AGGCC CTCCA CAATC
ACTAC ACCCA GAAGA GCCTG AGCCT GTCCC TGGGC AAG
```

Polynucleotide encoding PanELR IgG4(PE)N297A Heavy Chain (SEQ ID NO: 9)

```
CAGGT GCAGC TGGTG CAGAG CGGCG CCGAG GTGAA GAAGC CCGGC GCCAG
CGTGA AAGTG AGCTG CAAGG CCAGC GGCTA CACCT TCACC AACTA CTGGA
TCGTG TGGGT GAGGC AGGCC CCCGG CCAGG GACTG GAGTG GATGG GCGAC
CTGTA TAGCG GGGGA GGCTA CACCT TCTAC AGCGA GAACT TCAAG GGCAG
GGTGA CCATG ACCAG GGACA CCAGC ACCAG CACCG TGTAC ATGGA GCTCA
GCAGC CTGAG GAGCG AGGAT ACAGC CGTGT ACTAT TGCGC CAGGA GCGGC
TACGA CAGAA CCTGG TTCGC CCACT GGGGG CAGGG CACCC TCGTG ACTGT
CAGCA GCGCC AGCAC CAAAG GCCCC TCTGT GTTCC CCCTG GCCCC CTGTA
```

-continued

GCAGG AGCAC CAGCG AGTCA ACCGC CGCCC TGGGC TGCCT GGTGA AAGAC
TACTT CCCTG AGCCC GTGAC CGTGA GCTGG AATAG CGGCG CACTG ACCAG
CGGCG TGCAC ACCTT TCCCG CCGTG CTGCA GTCTA GCGGC CTGTA CAGCC
TGAGC TCAGT GGTGA CCGTG CCCAG CAGCA GCCTG GCAC CAAGA CCTAC
ACCTG CAACG TGGAC CACAA GCCCA GCAAC ACCAA GGTGG ACAAG CGGGT
GGAAA GCAAG TACGG CCCCC CTTGC CCCCC CTGCC CCGCA CCCGA GTTCG
AGGGC GGCCC AAGCG TGTTC CTGTT TCCCC CAAG CCCAA GGACA CCCTG
ATGAT CAGCA GGACC CCCGA GGTGA CTTGC GTGGT GGTGG ACGTG TCCCA
GGAGG ACCCC GAGGT GCAGT TCAAC TGGTA CGTGG ACGGC GTGGA AGTGC
ACAAC GCCAA GACCA AGCCC AGGGA GGAGC AGTTC GCCAG CACCT ACAGG
GTGGT CAGCG TCCTG ACCGT GCTGC ACCAG GACTG GCTGA ACGGC AAGGA
GTACA AGTGC AAGGT GAGCA ACAAG GGCCT GCCCA GCAGC ATCGA AGAA
CCATC AGCAA GGCCA AGGGA CAGCC CAGGG AGCCC CAGGT GTACA CACTG
CCCCC CAGCC AGGAA GAGAT GACCA AGAAC CAGGT GAGCC TGACC TGCCT
GGTGA AGGGC TTCTA CCCCA GCGAC ATTGC CGTCG AGTGG GAGAG CAACG
GCCAG CCCGA GAACA ACTAC AAGAC CACCC CACCT GTCCT GGATA GCGAC
GGCAG CTTCT TCCTG TACAG CAGGC TGACC GTGGA CAAGA GCAGG TGGCA
GGAGG GCAAC GTGTT CAGCT GCAGC GTGAT GCACG AGGCC CTGCA CAACC
ACTAC ACCCA GAAGA GCCTG AGCCT CTCCC TGGGC AAG

Polynucleotide encoding PanELR IgG4(PE)N297S Heavy Chain
(SEQ ID NO: 10)
CAGGT CCAGC TGGTG CAGAG CGGCG CCGAA GTGAA GAAAC CCGGC GCTAG
CGTGA AGGTG AGCTG CAAGG CCAGC GGCTA CACCT TCACC AACTA CTGGA
TCGTG TGGGT CAGGC AGGCC CCCGG CCAGG GCCTG GAGTG GATGG GCGAC
CTGTA CTCAG GCGGC GGCTA CACCT TCTAC AGCGA GAACT TCAAG GGCAG
GGTGA CCATG ACCAG GGATA CCAGC ACCAG CACCG TGTAC ATGGA GCTGA
GCAGC CTGAG GAGCG AGGAC ACTGC CGTGT ACTAT TGCGC CAGGA GCGGC
TACGA CAGGA CCTGG TTTGC CCACT GGGGA CAGGG CACCC TGGTG ACCGT
CAGCT CTGCC TCAAC CAAGG GCCCC TCAGT GTTCC CTCTG GCCCC TGTA
GCAGG AGCAC CAGCG AGAGC ACCGC CGCCC TGGGC TGCCT GGTGA AGGAC
TACTT CCCCG AGCCC GTGAC CGTGA GCTGG AATAG CGGGG CTCTG ACTAG
CGGAG TGCAC ACCTT CCCCG CCGTC CTGCA GTCTA GCGGC CTGTA TAGCC
TGAGC AGCGT GGTCA CCGTG CCAAG CAGCA GCCTG GCAC CAAGA CCTAC
ACCTG CAACG TGGAC CACAA GCCCA GCAAC ACAAA GGTGG ACAAG AGGGT
GGAGT CCAAG TACGG CCCCC CCTGC CCTCC CTGCC CCGCA CCCGA GTTCG
AGGGC GGCCC CTCCG TGTTT CTGTT CCCCC CAAA CCCAA GGACA CCCTG
ATGAT CAGCA GGACC CCCGA GGTGA CTTGC GTGGT GGTGG ACGTG AGCCA
GGAGG ACCCC GAGGT GCAGT TCAAC TGGTA CGTGG ACGGC GTGGA GGTGC
ACAAC GCCAA AACCA AGCCC AGGGA GGAGC AGTTC AGCAG CACCT ACAGG
GTGGT GAGCG TGCTG ACCGT GCTGC ACCAG GACTG GCTCA ACGGC AAGGA
GTACA AGTGC AAGGT GAGCA ACAAG GGCCT GCCCA GCAGC ATCGA AGAA
CCATC AGCAA GGCCA AGGGC CAGCC CAGAG AGCCA CAGGT GTACA CACTG -continued

```
CCCCC CAGCC AGGAG GAGAT GACCA AGAAC CAGGT GAGCC TGACC TGCCT

GGTGA AGGGC TTCTA CCCCA GCGAC ATCGC CGTGG AGTGG GAAAG CAACG

GCCAG CCCGA GAACA ACTAC AAGAC CACCC CCCCC GTGCT CGATA GCGAC

GGCAG CTTCT TCCTG TACAG CCGCC TGACC GTGGA CAAGA GCAGG TGGCA

GGAAG GCAAC GTGTT CAGCT GCAGC GTGAT GCACG AGGCC CTCCA CAACC

ACTAC ACCCA GAAGA GCCTG AGCCT GAGCC TGGGC AAG
```

---

What is claimed is:

1. An isolated antibody comprising heavy and light chains comprising polypeptides of SEQ ID NO:4 and SEQ ID NO:2, respectively.

2. An isolated antibody comprising heavy and light chains comprising polypeptides of SEQ ID NO:5 and SEQ ID NO:2, respectively.

3. A method of treating or ameliorating in a human ulcerative colitis, Crohn's disease, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, respiratory syncytial virus, flu, Behcets disease, uveitis, periodontal disease particularly gingivitis, exacerbation of asthma and COPD, cystic fibrosis, acne, Bronchiolitis obliterans syndrome, diffuse panbronchiolitis, deep vein thrombosis, preeclampsia, vasculitis, familial Mediterranean fever, reperfusion injury, pain and/or endometriosis comprising administering an effective amount of an isolated antibody comprising heavy and light chains comprising polypeptides of SEQ ID NO:4 and SEQ ID NO:2, respectively; or an isolated antibody comprising heavy and light chains comprising polypeptides of SEQ ID NO:5 and SEQ ID NO:2, respectively.

4. A pharmaceutical composition comprising an antibody of claim 1 in combination with one or more pharmaceutically acceptable carriers.

5. A pharmaceutical composition comprising an antibody of claim 2 in combination with one or more pharmaceutically acceptable carriers.

* * * * *